US007259186B2

(12) United States Patent
Cink et al.

(10) Patent No.: US 7,259,186 B2
(45) Date of Patent: Aug. 21, 2007

(54) SALTS OF FENOFIBRIC ACID AND PHARMACEUTICAL FORMULATIONS THEREOF

(75) Inventors: Russell Drew Cink, Grayslake, IL (US); Joseph B. Paterson, Jr., Vernon Hills, IL (US); Yi Gao, Vernon Hills, IL (US); Geoff G. Z. Zhang, Libertyville, IL (US); Michelle A. Long, Libertyville, IL (US); John B. Morris, Grayslake, IL (US); Joerg Rosenberg, Ellerstadt (DE)

(73) Assignee: Abbott Laboratories, Abbott Park, IL (US)

( * ) Notice: Subject to any disclaimer, the term of this patent is extended or adjusted under 35 U.S.C. 154(b) by 388 days.

(21) Appl. No.: 10/880,851

(22) Filed: Jun. 30, 2004

(65) Prior Publication Data

US 2005/0148594 A1    Jul. 7, 2005

Related U.S. Application Data

(63) Continuation-in-part of application No. PCT/EP03/14331, filed on Dec. 16, 2003.

(60) Provisional application No. 60/499,285, filed on Aug. 29, 2003, provisional application No. 60/499,284, filed on Aug. 29, 2003, provisional application No. 60/453,694, filed on Dec. 17, 2002.

(51) Int. Cl.
*A61K 31/19*   (2006.01)
*A61K 31/495*  (2006.01)
*C07C 59/76*   (2006.01)
*C07D 241/02*  (2006.01)

(52) U.S. Cl. ............. 514/571; 514/252.12; 562/460; 544/358

(58) Field of Classification Search ............. 562/460; 544/358; 514/571, 252.12
See application file for complete search history.

(56) References Cited

U.S. PATENT DOCUMENTS

| 2,799,241 | A  | 7/1957  | Wurster          |
|-----------|----|---------|------------------|
| 3,133,132 | A  | 5/1964  | Loeb et al.      |
| 3,173,876 | A  | 3/1965  | Zobrist          |
| 3,276,588 | A  | 10/1966 | Rosaen           |
| 3,541,005 | A  | 11/1970 | Strathmann et al.|
| 3,541,006 | A  | 11/1970 | Bixler et al.    |
| 3,546,142 | A  | 12/1970 | Michaels et al.  |
| 3,845,770 | A  | 11/1974 | Theeuwes et al.  |
| 3,907,792 | A  | 9/1975  | Mieville         |
| 3,914,286 | A  | 10/1975 | Mieville         |
| 3,916,899 | A  | 11/1975 | Theeuwes et al.  |
| 4,058,552 | A  | 11/1977 | Mieville         |
| 4,072,705 | A  | 2/1978  | Mieville         |
| 4,088,864 | A  | 5/1978  | Theeuwes et al.  |
| 4,160,020 | A  | 7/1979  | Ayer             |
| 4,179,515 | A  | 12/1979 | Mieville         |
| 4,200,098 | A  | 4/1980  | Ayer et al.      |
| 4,233,298 | A  | 11/1980 | Mieville         |
| 4,235,896 | A  | 11/1980 | Mieville         |
| 4,340,585 | A  | 7/1982  | Borzatta et al.  |
| 4,372,954 | A  | 2/1983  | Moreau et al.    |
| 4,574,080 | A  | 3/1986  | Roswall et al.   |
| 4,800,079 | A  | 1/1989  | Boyer            |
| 4,803,081 | A  | 2/1989  | Falk et al.      |
| 4,859,703 | A  | 8/1989  | Krause           |
| 4,895,726 | A  | 1/1990  | Curtet et al.    |
| 5,179,097 | A  | 1/1993  | Angres           |
| 5,286,497 | A  | 2/1994  | Hendrickson et al.|
| 5,573,776 | A  | 11/1996 | Harrison et al.  |
| 5,737,320 | A  | 4/1998  | Madonna          |
| 6,074,670 | A  | 6/2000  | Stamm et al.     |
| 6,277,405 | B1 | 8/2001  | Stamm et al.     |
| 6,284,803 | B1 | 9/2001  | Kothrade et al.  |
| 6,514,531 | B1 | 2/2003  | Alaux et al.     |
| 2001/0006662 | A1 | 7/2001 | Krill et al.    |
| 2003/0077297 | A1 | 4/2003 | Chen et al.     |
| 2005/0008704 | A1 | 1/2005 | Ray et al.      |
| 2005/0101561 | A1 | 5/2005 | Tunac et al.    |
| 2005/0148594 | A1 | 7/2005 | Cink et al.     |

OTHER PUBLICATIONS

"Guidline for the photostability testing of new drug substances and prodrugs," International Conference on Harmonization. Federal Register 65(95):27115-22 (1997).
*Photochemical Reactions.* In Stephen R. Byrn, Ralph R. Pfieffer and Joseph G. Stowell ed. Solid-State Chemistry of Drugs, 2$^{nd}$ edition, SSCI, Inc., West Lafayette, Indiana, 1999. pp. 391-416.
USP vol. 25, chapter 776, published by the United States Pharmacopeia (2002).
Albini, et al., "Photochemistry of drug," In Nalwa, Hari Singh.ed. Handbook of Photochemistry and Photobiology, American Scientific Publishers, Stevenson Ranch, Calif, 147-193 (2003). (CODEN: 69ENDV Conference; General Review written in English. CAN 140:344560 AN 2003:744654 CAPLUS).
Albini, et al., "Photochemistry of drugs: and overview and practical problems," Special Publication—Royal Society of Chemistry, 225 (Drugs: Photochemistry and Photostability), 1-73 (1998). (CODEN: SROCDO ISSN: 0260-6291. General Review written in English. CAN 130:57040 AN 1998:637767 CAPLUS).
Cohen, et al., "Structure-sensitive reactions of organic crystals," Proc. Intern. Symp. Reactivity solids, 4$^{th}$ Amsterdam, 1961, vol. date 1960, 556-562.

(Continued)

*Primary Examiner*—Barbara P. Badio
(74) *Attorney, Agent, or Firm*—Gregory W. Steele

(57) ABSTRACT

In one aspect, the present invention relates to a formulation in the form of molecular dispersion comprising i) fenofibric acid, a physiologically acceptable salt or derivative thereof and optionally other active substances, ii) a binder component comprising at least one enteric binder, and optionally iii) other physiologically acceptable excipients.

In a second aspect, the present invention relates to novel salts of fenofibric acid that are photostable when compared to other salts of fenofibric acid.

15 Claims, No Drawings

OTHER PUBLICATIONS

El-Shafei, et al., "Semi-empirical molecular orbital methods in the design of organic colorants," AATCC Review (2001), 1(12), 23-26. CODEN: ARAEBW ISSN: 1532-8813. Journal written in English. CAN 137:34449 AN 2002:38338 CAPLUS.

Greenhill, J. V. (Department Chemistry, University Florida, Gainesville, FL, USA). "Is the photodecomposition of drugs predictable?" In Toennesen, Hanne Hjorth ed: Photostability of Drugs and Drug Formulations, [International Meeting on Photostability of Drugs], 1st, Oslo, Jun. 1995 (1996), Meeting Date 1995, 83-110. Publisher: Taylor & Francis, London, UK CODEN: 63MKAH Conference; General Review written in English. CAN 125:284474 AN 1996:647343 CAPLUS.

Harris, et al., "Probing polymorphism and reactivity in the organic solid state using carbon-13 NMR spectroscopy: studies of p-Formyl-trans-cinnamic acid." J. of Solid State Chemistry. 94(1):197-205 (1991).

Liu, et al., "Inclusion of acitretin into cyclodextrins: Phase solubility, photostability, and physicochemical characterization," Department of Pharmacy, National University of Singapore, Singapore. Journal of Pharmaceutical Sciences, 92(12): 2449-2457 (2003).

Matsuda et al., "Physicochemical characterization of furosemide modifications," International J. Pharmaceutics, 60(1):11-26 (1990).

Matsuda, et al., "Pharmaceutical evaluation fo carbamazepine modifications: comparative study for photostability of carbarmazepine polymorphs by using Fourier-transformed reflection-absorption infrared spectroscopy and colorimetric measurement." J. of Pharmacy and Pharmacology, 46(3): 162-167 (1994).

Najanishi, et al., "Preparation of p-phenylenediacrylic acid salts and their photoreaction in the solid state." Kenkyu Hokoku—Sen'I Kobunshi Zairyo Kenkyusho, 133:39-43 (1982) English Abstract Only.

Nord, K., Andersen, H., Tonnesen, H.H. *Photoreactivity of biologically active compounds. XII. Photostability of polymorphic modifications of chloroquine diphosphate*. Drug Stability, 1(4):243-248, 1997.

Price, S.L., "The computational predication of pharmaceutical crystal structures and polymorphism," Advanced Drug Delivery Reviews, 56:301-319 (2004).

Tonnesen, H.H, et al., *"Photoreactivity of biologically active compounds. XIII. Photostability of mefloquine hydrochlorice in the solid state"*, Drug Stability, 1(4), 249-253, 1997.

SALTS OF FENOFIBRIC ACID AND PHARMACEUTICAL FORMULATIONS THEREOF

RELATED APPLICATION INFORMATION

This application is a continuation-in-part application of PCT/EP03/14331 filed on Dec. 16, 2003 which claims priority to U.S. Ser. No. 60/453,694, filed on Dec. 17, 2002, each of which are incorporated by reference.

This application also claims priority to U.S. Ser. No. 60/499,284 filed on Aug. 29, 2003 and U.S. Ser. No. 60/499,285 filed on Aug. 29, 2003, each of which are incorporated by reference.

FIELD OF THE INVENTION

In one aspect, the present invention relates to pharmaceutical formulations comprising fenofibric acid, a physiologically acceptable salt or derivative thereof, processes of making said formulations, such as by melt extrusion, and the use of these formulations for the oral administration of fenofibric acid, a physiologically acceptable salt or derivative thereof.

In a second aspect, the present invention relates to novel salts of fenofibric acid that exhibit photostability when compared to other salts of fenofibric acid. These photostable salts are useful for pharmaceutical formulations in a form of molecular dispersions that contain at least one of these novel salts. These novel salts can be used to treat hyperlipidemia or coronary heart diseases.

BACKGROUND OF THE INVENTION

Fenofibrate is a well-known lipid regulating agent which has been commercially available for a long time.

Fenofibrate is usually orally administered. After its absorption, which is known to take place in the duodenum and other parts of the gastrointestinal tract, fenofibrate is metabolized in the body to fenofibric acid. In fact, fenofibric acid represents the active ingredient of fenofibrate. In other words, fenofibrate is a so-called prodrug which is converted in vivo to the active molecule. After oral administration of fenofibrate, fenofibric acid is found in plasma.

U.S. Pat. Nos. 4,179,515 and 4,235,896 disclose the preparation of fenofibric acid and also describe acid addition salts of amine containing analogs. U.S. Pat. No. 4,372,954 discloses the moroxydine salt of fenofibric acid as useful for the inhibition of platelet aggregation and for lowering fibrinogen. Spanish patent ES 474039 discloses the use of the cinnarizine-salt of fenofibric acid for the reduction of triglyceride levels and the sodium salt of fenofibric acid (in solution) has also been disclosed (Bosca et al., *Photochemistry and Photobiology*, 1999, 70(6), 853–857).

Fenofibrate is known to be nearly insoluble in water and requires special pharmaceutical formulations in order to ensure good bioavailability, especially after oral administration. Accordingly, fenofibrate has been prepared in several different formulations, (see WO 00/72825 and the citations provided therein, such as U.S. Pat. Nos. 4,800,079, 4,895, 726, 4,961,890, EP-A 0 793 958 and WO 82/01649). Additional formulations of fenofibrate are described in WO 02/067901 and citations provided therein, such as U.S. Pat. Nos. 6,074,670 and 6,042,847.

The fenofibrate products currently on the market involve a formulation comprising a micronized drug substance in capsules and/or tablets. However, the insolubility of fenofibrate in water may still negatively impact the in vivo performance of the product. One approach to mitigate the bioavailability issue is to render the crystalline drug amorphous, leading to accelerated drug release. However, recrystallization of amorphous materials could occur, especially for insoluble molecules such as fenofibrate.

Thereupon, one object of the present invention is to provide pharmaceutical formulations that make fenofibric acid sufficiently bioavailable and prevent recrystallization of the active substance. This object is achieved by formulations that comprise fenofibric acid, a physiologically acceptable salt or a physiologically acceptable derivative thereof that is embedded in an enteric binder.

It is another object of the present invention to provide novel salts of fenofibric acid that result in a product having improved photostability when compared to fenofibric acid and other salts of fenofibric acid.

SUMMARY OF THE INVENTION

In one aspect, the present invention relates to a pharmaceutical formulation comprising:

i) fenofibric acid, or a physiologically acceptable salt or derivative thereof and optionally, other active ingredients (which is collectively referred to as the "active substance component);

ii) a binder component comprising at least one enteric binder; and optionally, iii) other physiologically acceptable excipients.

The physiologically acceptable derivative of fenofibric acid can be fenofibrate. Additionally, the fenofibric acid, physiologically acceptable salt or derivative thereof can be present in the formulation as a molecular dispersion.

The binder employed in the above-described formulation can be an enteric polymer, such as those selected from the group consisting of: hydroxypropylmethylcellulose phthalate, hydroxypropylmethylcellulose acetate succinate, carboxymethylethylcellulose, cellulose acetate phthalate, cellulose acetate trimellitate and carboxymethylcellulose sodium.

Additionally, the enteric polymer can be a copolymer, such as a copolymer of (meth)acrylic acid and at least one alkyl (meth)acrylic acid ester. The alkyl (meth)acrylic acid ester can be methyl methacrylate. The copolymer can have a ratio of free carboxyl groups to esterified carboxyl groups of about 2:1 to 1:3, preferably, about 1:1.

The other physiologically acceptable excipients can be a flow regulator, such as a highly dispersed silica gel.

Preferably, the above-described formulation comprises i) about 5 to about 60% by weight, preferably about 7 to about 40% by weight and most preferably, about 10 to about 30% by weight of active substance component; ii) about 20 to about 95% by weight, preferably about 30 to about 90% by weight and most preferably, about 40 to about 80% by weight, of a binder component; iii) 0 to about 75% by weight, preferably about 1 to about 60% by weight and most preferably, about 5 to about 40% by weight, of other physiologically acceptable excipients. It is preferred that the enteric binder employed in the above-described formulation comprise about 5 to about 95% by weight, more preferably from about 10 to about 70% by weight and most preferably, about 30 to about 60% by weight of the binder component (ii). Moreover, the content of the active substance component (i) relative to the binder component (ii) is from about 1 to about 50% by weight, preferably about 10 to about 40% by weight and most preferably about 20 to about 30% by weight.

The above-described formulation can be obtained by melt extrusion of a mixture comprising fenofibric acid, a physiologically acceptable salt or derivative thereof, binder and optionally, other active substances and/or physiologically acceptable excipients.

The above-described formulation can be used in a method of oral administration of fenofibric acid, a physiologically acceptable salt or derivative thereof. This method involves the step of administering the above-described formulation and optionally, other excipients, as a dosage form to a mammal, preferably a human.

In another aspect, the present invention relates to a salt of fenofibric acid selected from the group consisting of choline, ethanolamine, diethanolamine, piperazine, calcium and tromethamine.

In yet another embodiment, the present invention relates to a pharmaceutical formulation in the form of a molecular dispersion comprising a salt of fenofibric acid that is selected from the group consisting of choline, ethanolamine, diethanolamine, piperazine, calcium and tromethamine and a binder component comprising at least one enteric binder. Preferably, said formulation comprises about 5 to about 60% by weight of one of said novel salts and about 20 to about 95% by weight of a binder component.

DETAILED DESCRIPTION OF THE INVENTION

The present invention will be described in two different aspects. Each of these two aspects of the present invention are treated separately under different headings for the convenience of the reader and should not be construed as limiting the present invention in any way. These headings are "Pharmaceutical Formulations of Fenofibric Acid, Physiologically Acceptable Salts or Derivatives Thereof" and "Novel Salts of Fenofibric Acid".

1. Pharmaceutical Formulations of Fenofibric Acid, Physiologically Acceptable Salts or Derivatives Thereof In one aspect, the present invention relates to pharmaceutical formulations, preferably solid formulations, comprising a mixture of:
 i) fenofibric acid, or a physiologically acceptable salt or derivative thereof and optionally other active substances;
 ii) a binder component comprising at least one enteric binder; and optionally
 iii) other physiologically acceptable excipients.

As used herein, the term "fenofibric acid" refers to 2-[4-(4-chlorobenzoyl)phenoxy]-2-methyl-propanoic-acid, having the following formula I

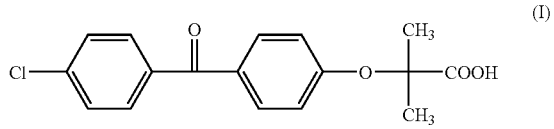

The physiologically acceptable salts of the present invention are preferably base addition salts. The base addition salts include salts with inorganic bases, including, but not limited to, metal hydroxides or carbonates of alkali metals, alkaline earth metals or transition metals, or with organic bases, including, but not limited to, ammonia, basic amino acids such as arginine and lysine, amines, e.g. methylamine, dimethylamine, trimethylamine, triethylamine, ethylamine, diethylamine, ethylenediamine, ethanolamine, diethanolamine, 1-amino-2-propanol, 3-amino-1-propanol or hexamethylenetetraamine, saturated cyclic amines having 4 to 6 ring carbon atoms, including, but not limited to, piperidine, piperazine, pyrrolidine and morpholine, and other organic bases, for example N-methylglucamine, creatine and tromethamine, and quaternary ammonium compounds, including, but not limited to, tetramethylammonium and the like. Salts with organic bases are preferably formed with amino acids, amines or saturated cyclic amines. Preferred salts with inorganic bases are preferable formed with Na, K, Mg and Ca cations.

The physiologically acceptable derivatives of the present invention are preferably carboxylic acid derivatives that are reconvertable in vivo to the free carboxylic acid. Thus, the preferred physiologically acceptable derivatives of fenofibric acid are prodrugs of fenofibric acid. The conversion of said prodrugs in vivo may occur under the physiological conditions that the prodrug experiences during its passage or may involve cleavage by enzymes, especially esterases, accepting the prodrug as substrate.

The physiologically acceptable derivatives of the present invention are fenofibric acid derivatives having the following formula II

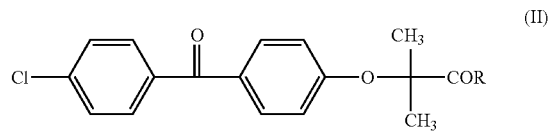

wherein R is $OR_1$, $-NR_1R_2$, $-NH$-alkylene-$NR_1R_2$ or $-O$-alkylene-$NR_1R_2$, with $R_1$ and $R_2$ being identical or different from each other and representing a hydrogen atom, alkyl, alkoxyalkyl, alkoyloxyalkyl, alkoxycarbonyl, aminoalkyl, alkylaminoalkyl, dialkylaminoalkyl, trialkylammoniumalkyl, cycloalkyl, aryl or arylalkyl substituted on the aromatic residue by one or more halogen, methyl or $CF_3$ groups, or $R_1$ and $R_2$ forming together with the nitrogen atom to which they are connected, a 5- to 7-membered aliphatic heterocyclic group which may enclose a second heteroatom selected from the group consisting of N, O, and S, and which may be substituted by one or more halogen, methyl or $CF_3$ groups. Particularly preferred physiologically acceptable derivatives are fenofibric acid esters, i.e., derivatives of formula II wherein R is $OR_1$ and $R_1$ is other than hydrogen. These esters include derivatives of formula II wherein $R_1$ in $-OR_1$ represents an alkyl group having from 1 to 6 carbon atoms, an alkoxymethyl group having from 2 to 7 carbon atoms, a phenylalkyl group composed of an alkylene group having from 1 to 6 carbon atoms and a phenyl group, a phenyl group, an acetoxymethyl group, a pivaloyloxymethyl group, an ethoxycarbonyl group and a dimethylaminoethyl group.

Especially preferred according to the present invention are alkyl esters of fenofibric acid.

In one embodiment, the present invention relates to formulations comprising i) the 1-methylethyl ester (isopropyl ester) of fenofibric acid, i.e. fenofibrate (INN).

The active substance (also known as the active pharmaceutical ingredient or "API") component i) of the formulations of the present invention comprise fenofibric acid, a physiologically acceptable salt or derivative thereof. Mixtures of one or more of these forms are possible. For reasons of simplicity, this part of the active substance component is hereinafter referred to as the "fenofibric acid content".

Besides the fenofibric acid content, component i) of the formulations may comprise other active substances, particularly those having an action like that of fenofibric acid, e.g. other lipid regulating agents, such as, but not limited to, further fibrates, e.g. bezafibrate, ciprofibrate and gemfibrocil, or statins, e.g. lovastatin, mevinolin, pravastatin, fluvastatin, atorvastatin, itavastatin, mevastatin, rosuvastatin, velostatin, synvinolin, simvastatin, cerivastatin and numerous others mentioned in, for instance, in WO 02/67901 and the corresponding citations therein as well as expedient active substances of other types. In one embodiment, the present invention comprises single-drug products that comprise an active substance component i) that essentially consists of fenofibric acid or a physiologically acceptable salt of fenofibric acid or a physiologically acceptable derivative of fenofibric acid or of a mixture thereof. As used with respect to the active substance, the term "essentially" refers to a percentage ratio of at least 90%, preferably of at least 95% and most preferably of at least 98%.

The active substance component ordinarily constitutes about 5 to about 60% by weight, preferably about 7 to about 40% by weight and, in particular, about 10 to about 30% by weight of the formulation. Data in % by weight are based, unless indicated otherwise, on the total weight of the formulation.

The formulation base of the formulations of the present invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

The binder component of the formulations of the present invention may also be understood to include a binder which at least in part forms a binder matrix, particularly, a polymer matrix, in which the active substance is embedded. Binders suitable for use in the present invention include, solid meltable solvents. The binder matrix serves to take up and, especially, to dissolve at least part of the active substance component, especially the fenofibric acid content. To this extent, the binder is also a solvent. In relation to the active substance which is in the form of a molecular dispersion and dissolved, it is possible to speak of a solid solution of the active substance in the binder, the binder being either in crystalline form or in amorphous form.

Preferably, the binder component is at least partly soluble or swellable in an aqueous media, expediently under the conditions of use, that is to say, in particular physiological conditions. An enteric binder may be defined as a binder, the solubility or swellability of which increases with increasing pH and vice versa. Particularly preferred are binders that are at least partly soluble or swellable in aqueous media having a pH of from about 5 to about 9, more preferably from about 6 to about 8 and most preferably from about 6.5 to about 7.5.

Within the framework of this present description, aqueous media include water and mixtures of water and other components that comprise at least 50% by weight, preferably at least 70% by weight and most preferably at least 90% by weight of water. Aqueous media include, but are not limited to, body fluids such as fluids of the digestive tract, e.g. gastric juices, intestinal juices and saliva, blood; aqueous vehicles for use in pharmaceutical formulations in the drugs and food supplement sectors, e.g. vehicles which can be administered orally or parenterally, such as drinking water or water for injections.

As used herein, "swelling" refers to a process in which the volume and/or shape of a solid body, such as, for example, a solid formulation of the present invention, changes on exposure to liquids, vapors and gases. Swellable or soluble polymers are preferably hydrophilic polymers that are able to accumulate water at least on the surface and/or take up water between the polymer chains, mainly by adsorption. Limited swelling usually results in gel formation, which is why polymers capable of limited swelling and usable according to the present invention can be selected from the polymers commonly known as gel formers. Unlimited swelling usually leads to the formation of solutions or colloidal solutions, which is why polymers capable of unlimited swelling and usable according to the present invention can be selected from the polymers which form at least colloidal solutions in a particular aqueous medium. It is expedient to take into account, especially in relation to body fluids, particularly those of the gastrointestinal tract, that there may be local variations in the physiological conditions, especially the pH. Since it is preferred, according to the present invention, that the active substance be taken up mainly in the duodenum, jejunum and/or ileum, it is preferable for the binder to be swellable or soluble under the conditions prevailing in the duodenum, jejunum and/or ilium. In particular, it is preferred that only slight or, preferably, essentially no swelling or dissolution of the polymer to take place in the preceding sections of the gastrointestinal tract, especially in the stomach.

It is preferred that at least one binder of the binder component be a polymeric material, particularly an enteric polymer. As used herein, the term "enteric polymer", which is a term of the art, refers to a polymer which is preferentially soluble in the less acid environment of the intestine relative to the more acid environment of the stomach. Enteric polymers are pH sensitive. Typically, the polymers are carboxylated and interact (swell) very little with water at low pH, while at high pH the polymers ionize, causing swelling, or dissolving of the polymer. Therefore, the binder component can be designed to remain intact in the acidic environment of the stomach (preventing recrystallization of the active substance in the stomach), but dissolve in the more alkaline environment of the intestine.

The enteric polymer may be made from a conventional material. It is preferred that at least one binder of the binder component be selected from enteric polymers such as, but not limited to, suitable cellulose derivatives, e.g. cellulose acetate phthalates, cellulose acetate succinates, cellulose acetate trimellitates, carboxyalkyl(alkyl)celluloses and hydroxyalkyl(alkyl) cellulose phthalates; suitable polyvinyl-based polymers and copolymers, e.g. polyvinylacetatephthalate, polyvinylbutyrate acetate, vinyl acetate-maleic anhydride copolymer, styrene-maleic mono-ester copolymer; and suitable acrylic/methacrylic polymers and copolymers, e.g. methyl acrylate-methacrylic acid copolymer, and methacrylate- methacrylic acid-octyl acrylate copolymer.

Preferred enteric binders are pharmaceutically acceptable acrylic and methacrylic acid polymers and copolymers. These include copolymers with anionic characteristics based on (meth)acrylic acid and alkyl (meth)acrylic acid esters such as, but not limited to, methyl (meth)acrylate. Preferably, these copolymers have weight average molecular weights of around 50,000 to 300,000, most preferably around 100,000 to 150,000, e.g. around 135,000. The ratio of free carboxyl groups to esterified carboxyl groups of said copolymers is preferably in the range of around 2:1 to 1:3, most preferably, 1:1 to 1:2. Specific examples of copolymers that can be used include the acrylic resins having the proprietary names Eudragit® L and S that are based on methacrylic acid and methyl methacrylate that have a ratio of free carboxyl groups to esterified carboxy groups of around 1:1 and 1:2, respectively. Among these, copolymers of the Eudragit® L type are preferred, most preferred is Eudragit® L 100, a pH dependent anionic polymer solubilizing above pH 6.0 for targeted drug delivery in the jejunum and Eudragit® S 100, a pH dependent anionic polymer solubilizing above pH 7.0 for targeted drug delivery in the ileum.

Other preferred enteric binders that can be used herein are pharmaceutically acceptable cellulose derivatives. These include, but are not limited to, carboxymethylethylcellulose (CMEC) and carboxymethylcellulose sodium (sodium cellulose glycolate), and particularly hydroxypropylmethylcellulose phthalate, especially hypromellose phthalates such as 220824 and 220731, hydroxypropylmethylcellulose acetate succinate (AQOAT), cellulose acetate phthalate (CAP), and cellulose acetate trimellitate (CAT). Such polymers are sold under the tradename Cellacefate® (cellulose acetate phthalate) from Eastman Chemical Co., Aquateric® (cellulose acetate phthalate aqueous dispersion) from FMC Corp., Aqoat® (hydroxypropylmethylcellulose acetate succinate aqueous dispersion), and HP50 and HP55 (hydroxypropylmethylcellolose phthalates) from ShinEtsu K. K. Additionally, enteric binders include casein.

These enteric binders may be used either alone or in combination, and optionally together with binders other than those mentioned above.

Thereupon, the binder component of the formulations of the present invention comprises at least one of the enteric binders described above and particularly, at least one enteric polymer. The binder component may comprise other binders of these types and/or of other types. The properties of the formulations of the present invention can be altered by the nature of the chosen binder(s) or the admixture of different binders. In particular, it is possible in this manner to control the release of active substance.

In another embodiment of the present invention, the binder component comprises of one of the enteric binders described above. In another embodiment of the present invention, the enteric binder component comprises a mixture of at least two of the enteric binders described above. In this case, the enteric binder(s) constitute(s) 100% by weight of the binder component (ii).

In yet a further embodiment of the present invention, the binder component comprises, in addition to one or more than one enteric binder, at least one other (non-enteric) binder. In this embodiment, the enteric binder preferably constitutes about 5 to about 95% by weight, more preferably about 10 to about 70% by weight and, most preferably, about 30 to about 60% by weight of the binder component (ii).

If at least one other (non-enteric) binder is present, it is preferred that said other (non-enteric) binder that is to be used in combination with the enteric binder be selected from the group consisting of: synthetic polymers such as, but not limited to, polyvinyllactams, in particular polyvinylpyrrolidone (PVP); copolymers of vinyllactams such as, but not limited to, N-vinylpyrrolidone, N-vinylpiperidone and N vinyl-ε-caprolactam, but especially N-vinylpyrrolidone, with (meth)acrylic acid and/or (meth)acrylic esters, such as, but not limited to, long-chain (meth)acrylates, e.g. stearyl (meth)acrylate, dialkylaminoalkyl (meth)acrylates, which may be quaternized, and maleic anhydride, vinyl esters, especially vinyl acetate, vinylformamide, vinylsulfonic acid or quaternized vinylimidazole; copolymers of vinyl acetate and crotonic acid; partially hydrolyzed polyvinyl acetate; polyvinyl alcohol; (meth)acrylic resins such as, but not limited to, poly(hydroxyalkyl (meth)acrylates), poly(meth) acrylates, acrylate copolymers; polyalkylene glycols such as, but not limited to, polypropylene glycols and polyethylene glycols, preferably with molecular weights above 1,000, more preferably above 2,000 and most preferably above 4,000 (e.g. polyethylene glycol 6,000); polyalkylene oxides such as, but not limited to, polypropylene oxides and, in particular polyethylene oxides, preferably of low molecular weight, especially with weight average molecular weights of less than 100,000; polyacrylamides; polyvinylformamide (where appropriate partially or completely hydrolyzed); modified natural polymers, e.g. modified starches and modified celluloses, such as, but not limited to, cellulose esters and, particularly, cellulose ethers, e.g. methylcellulose and ethylcellulose, hydroxyalkylcelluloses, in particular hydroxypropylcellulose, hydroxyalkylalkylcelluloses, particularly hydroxypropylmethylcellulose or hydroxypropylethylcellulose; starch degradation products, particularly, starch saccharification products, such as maltodextrin; natural or predominantly natural polymers such as, but not limited to, gelatin, polyhydroxyalkanoates, e.g. polyhydroxybutyric acid and polylactic acid, polyamino acids, e.g. polylysine, polyasparagine, polydioxanes and polypeptides, and mannans, especially galactomannans; and nonpolymeric binders such as, but not limited to, polyols, for example those described in WO 98/22094 and EP 0 435 450, in particular sugar alcohols such as, but not limited to, maltitol, mannitol, sorbitol, cellobiitol, lactitol, xylitol and erythritol, and isomalt (Palatinit).

Of the aforementioned binders, the polymeric binders, particularly, the modified natural polymers, especially modified starches and cellulose ethers, and particularly, the synthetic polymers, especially polyvinylpyrrolidone and copolymers of vinyllactams, are preferred.

It is particularly preferred that at least one other binder of the binder component be selected from polyvinylpyrrolidones, e.g. Kollidong® K25, N-vinylpyrrolidone/vinyl acetate copolymers, especially copovidone, e.g. Kollidon® VA 64, and low molecular weight cellulose derivatives such as low molecular weight hydroxypropylcellulose, e.g. Klucel®EF with weight average molecular weights of about 45,000 to about 70,000 or about 80,000, and low molecular weight hydroxypropylmethylcellulose, e.g. Methocel® E3, E5 and E7.

Binder components that are preferred for the process are those which are melt-processable.

Polymers that can be used as polymeric binders are those which have a K value (according to H. Fikentscher, *Cellulose-Chemie* 13 (1932), pp. 58–64 and 71–74) in the range between 10 and 100, preferably, between 15 and 80.

In a preferred embodiment, the binder component has a glass transition temperature of more than about 80° C., preferably more than about 90° C. and most preferably of more than about 100° C. In addition, the suitability of glass transition temperatures in this range is governed by the necessary melt-processability of the binder or binder-containing mixtures.

The content of the binder component (ii) in the formulation of the present invention is ordinarily from about 20 to about 95% by weight, preferably about 30 to about 90% by weight and most preferably about 40 to about 80% by weight.

In a particular embodiment, the present invention relates to formulations wherein the fenofibric acid, a physiologically acceptable salt or derivative thereof is in the form of a molecular dispersion.

The term "molecular dispersion" as used herein and as known to one skilled in the art, describes systems in which a substance, in the present case at least part and particularly the predominant part of the fenofibric acid content, is homogeneously dispersed in the binder component. In a molecular dispersion, the dispersed substance is free of interfaces. In this case, the binder usually forms a matrix which, according to the present invention, is formed by the binder component or at least by a predominant part of the binder component, advantageously, the enteric binder.

According to this embodiment, the content of active substance crystals in a formulation of the present invention is preferably below about 15% and most preferably, below about 10%. Statements about crystal contents relate to the total amount of the active substance(s), particularly, the fenofibric acid content.

A formulation of the present invention that is essentially free of active substance crystals represents a particular embodiment of the present invention. The reduction in the crystal content is associated with an increase in the homogenization of the active substance in the matrix.

Molecular dispersion systems are, according to a particular embodiment, solid at room temperature (about 25° C.), but melt-processable at higher temperatures.

Formulations of the present invention in which there is no crystalline contents for essentially any constituent (essentially amorphous or crystal-free formulations) represent an additional embodiment of the present invention.

The state of such molecular dispersions can be investigated using known analytical methods, e.g. by differential scanning calorimetry (DSC) or wide-angle X-ray scattering measurements (WAXS measurements). Measurement of a molecular dispersion in DSC analysis lacks the usually endothermic, peak due to melting that occurs with the crystalline pure substance. Another possibility for identifying a molecular dispersion is the reduction in intensity and/or absence of typical X-ray diffraction signals in WAXS analysis.

For the purpose of forming molecular dispersions and, in particular, solid solutions by at least part of the active substance component in the binder component, the content of active substance component based on the binder component is present from about 1 to about 50% by weight, preferably about 10 to about 40% by weight and more preferably about 20 to about 30% by weight.

Formulations of the present invention may contain, in addition to a binder component, further physiologically acceptable excipients (excipient component iii). Such excipients may facilitate the production of the formulation and/or modulate its properties. The nature and amount are chosen so that they do not impair development of the special properties of the formulations of the present invention or contribute to destabilizing this system.

Excipients are usually conventional pharmaceutical excipients, for example, fillers such as, but not limited to, sugar alcohols, e.g. lactose, microcrystalline cellulose, mannitol, sorbitol and xylitol, isomalt (cf. DE 195 36 394), starch saccharification products, talc, sucrose, cereal corn or potato starch, where present in a concentration of about 0.02 to about 50, preferably about 0.20 to about 20% by weight based on the total weight of the mixture; lubricants, glidants and mold release agents such as, but not limited to, magnesium, aluminum and calcium stearates, talc and silicones, and animal or vegetable fats, especially in hydrogenated form and those which are solid at room temperature. These fats preferably have a melting point of 30° C. or above. Technically preferred in relation to the melt extrusion process are, as described in DE 197 31 277, triglycerides of $C_{12}$, $C_{14}$, $C_{16}$ and $C_{18}$ fatty acids or, to improve the processing properties, sodium stearylfumarate, lecithin, as described in connection with the extrusion of an isomalt-containing polymer/active substance melt in DE 195 36 394. It is also possible to use waxes such as, but not limited to, carnauba wax. These fats and waxes may be admixed alone or together with mono- and/or diglycerides or phosphatides, particularly, lecithin. The mono- and diglycerides are preferably derived from the abovementioned fatty acid types. Where present, the total amount of excipients in the form of lubricants and mold release agents is preferably about 0.1 to about 10% by weight and, more preferably, about 0.1 to about 2% by weight, based on the total weight of the mixture; flow regulators, e.g. colloidal silica (highly dispersed silicon dioxide), especially the high-purity silicon dioxides having the proprietary name Aerosil®, where present, in an amount of about 0.1 to about 5% by weight based on the total weight of the mixture; dyes such as, but not limited to, azo dyes, organic or inorganic pigments or dyes of natural origin, with preference being given to inorganic pigments e.g. iron oxides, where present, in a concentration of about 0.001 to about 10, preferably about 0.1 to about 3% by weight, based on the total weight of the mixture; stabilizers such as, but not limited to, antioxidants, light stabilizers, hydroperoxide destroyers, radical scavengers, stabilizers against microbial attack; plasticizers, especially those described below.

It is also possible to add wetting agents, preservatives, disintegrants, adsorbents and mold release agents, and surfactants, especially anionic and nonionic, such as, for example, soaps and soap-like surfactants, alkyl sulfates and alkylsulfonates, salts of bile acids, alkoxylated fatty alcohols, alkoxylated alkylphenols, alkoxylated fatty acids and fatty acid glycerol esters, which may be alkoxylated, and solubilizers such as Cremophor® (polyethoxylated castor oil), Gelucire® and Labrafil® vitamin E TPGS and Tween® (ethoxylated sorbitan fatty acid esters) (cf., for example, H. Sucker et al. *Pharmazeutische Technologie*, Thieme-Verlag, Stuttgart 1978).

Excipients, for the purpose of the present invention, also refers to substances for producing a solid solution with the active substance. Examples of these excipients are pentaerythritol and pentaerythritol tetraacetate, urea, phosphatides such as lecithin, polymers such as, for example, polyethylene oxides and polypropylene oxides and their block copolymers (poloxamers) and citric and succinic acids, bile acids, stearins and others as indicated, for example, by J. L. Ford, *Pharm. Acta Helv.* 61, (1986), pp. 69–88.

Also regarded as pharmaceutical excipients are additions of acids and bases to control the solubility of an active substance (see, for example, K. Thoma et al., *Pharm. Ind.*, 51, (1989), pp. 98–101).

Excipients as used in the present invention also include vehicles specific for the dosage form, i.e. appropriate for a particular dosage form, in particular peroral and, especially, tablets and capsules, also low-melting or liquid excipients such as polyalkylene glycols of low molecular weight, such as polyethylene glycol and/or polypropylene glycol with weight average molecular weights of less than about 1,000, water or suitable aqueous systems.

It is also possible to add excipients such as, but not limited to, masking flavors and odor-masking agents, particularly, sweeteners and odorants.

Further particular embodiments involving excipients are known to those skilled in the art as described, for example, in Fiedler, H. B., Lexikon der Eilfsstoffe fir Fharmazie, Kosmetik, and angrenzende Gebiete, 4th edition, Aulendorf: ECV-Editio-Cantor-Verlag (1996).

The only requirement for the suitability of the excipients is usually the compatibility with the active substances and excipients used. The excipients ought not to impair the formation of molecular dispersions.

The excipient component in solid formulations of the present invention preferably comprises at least one of the excipients described above. It may comprise other excipients of these types and/or other types.

One embodiment of the present invention comprises formulations with excipient component iii). In this embodiment, the content of the other physiologically acceptable excipients in the formulations of the present invention can be up to about 75% by weight, preferably up to about 60% by weight and, more preferably, up to about 40% by weight.

A particular embodiment of the present invention comprises formulations which comprise:
 i) fenofibric acid or fenofibrate;
 ii) at least one binder selected from enteric polymers; and
 iii) optionally, other physiologically acceptable excipients, in particular a flow regulator, e.g. highly disperse silica gel.

The formulations of the present invention preferably contain less than about 7% by weight and, more preferably, less than about 4% by weight of water. A preferred embodiment is represented by less than about 2% by weight of water.

From the viewpoint of a formulation that can be administered orally, it is particularly preferred for at least part of the binder component to be designed such that the release of active substance at acidic pH is delayed and recrystallization of the active in the stomach prevented.

The formulations of the present invention have a solid consistency. As used herein, the term "solid" has in this connection the meaning assigned to it in the relevant pharmacopeias in connection with pharmaceutical preparations. In the wider sense, solid formulations of the present invention also include those with a semisolid consistency, which may result in formulations having a high fenofibrate content. These formulations are viscous or highly viscous formulations that can be molded at room temperature. The suitability of semisolid formulations for being expediently processed, according to the present invention by means of extrusion, is important.

The present invention also relates to the use of formulations of the present invention as dosage forms, particularly for oral administration of fenofibric acid or a physiologically acceptable salt or derivative thereof.

Accordingly, formulations of the present invention are mainly used in the physiological practice, particularly, in the medical sector for humans and animals. In this sense, the formulations are used as or in dosage forms, i.e. the formulations of the present invention have expedient forms that are appropriate for physiological practice, if necessary together with other excipients.

Thus, the term "dosage form" refers to any dosage form that is suitable for administration of active substances to an organism, particularly to mammals, preferably humans, agricultural or domestic animals.

Conventional dosage forms include, but are not limited to, (in alphabetical sequence) capsules, granules, pellets, powders, suspensions, suppositories, tablets.

Granules comprise solid grains of the formulations of the present invention, wherein each grain represents an agglomerate of powder particles. Granules can have a mean corn size in the range of about 0.12 to about 2 mm, preferably about 0.2 to about 0.7 mm. Granules are preferably intended for oral use as dosage forms. The user can be offered single-dose preparations, for example, granules packed in a small bag (sachet), a paper bag or a small bottle, or multi-dose preparations which require appropriate measuring. However, in many cases, such granules do not represent the actual dosage form, but are intermediates in the manufacture of particular dosage forms, for example, tablet granules to be compressed to tablets, capsule granules to be packed into hard gelatin capsules, or instant granules or granules for oral suspension to be put in water before intake.

As capsules, the formulations of the present invention are usually packed into a hard shell composed of two pieces fitted together or a soft, one-piece, closed shell, which may vary in shape and size. It is possible for the formulations of the present invention to be encased or enveloped or embedded in a matrix in suitable polymers, that is to say, microcapsules and microspherules. Hard and soft capsules comprise mainly of gelatin, while the latter can have a suitable content of plasticizing substances such as glycerol or sorbitol. Hard gelatin capsules are used to receive preparations of the present invention that have a solid consistency, for example granules, powder or pellets. Soft gelatin capsules are suitable for formulations with a semisolid consistency and, if required, also viscous liquid consistency.

Pellets are granules of formulations of the present invention in the particle size ranging from about 0.5 to about 2.0 mm in diameter. Pellets having a narrow particle size distribution, preferably from about 0.8 to about 1.2 mm, and with an essentially round shape, are preferred.

In semisolid preparations, formulations of the present invention are taken up in a suitable vehicle. Appropriate bases are known to those skilled in the art.

Suppositories are solid preparations for rectal, vaginal or urethral administration. In order to be appropriate for this route of administration, formulations of the present invention in these drug forms must be taken up in suitable vehicles, for example, in fats which melt at body temperature, such as hard fat, macrogols, i.e. polyethylene glycols with molecular weights of about 1000 to about 3000 in various proportions, glycerol, gelatin and the like.

Tablets are solid preparations for oral use. The meaning of oral within the framework of the present invention is, particularly, that of the term "peroral", i.e. tablets for absorption or action of the active substance in the gastrointestinal tract. Particular embodiments include, but are not limited to, coated tablets, layered tablets, laminated tablets, tablets with modified release of active substance, matrix tablets, effervescent tablets or chewable tablets. The formulations of the present invention usually comprise at least a part of the necessary tablet excipients, such as binders, fillers, glidants and lubricants, and disintegrants. Tablets of formulations of the present invention may also, if necessary, comprise other suitable excipients.

Excipients which assist tableting, for example lubricants and glidants, for example those mentioned above, with preference for flow regulators such as silica and/or lubricants such as magnesium stearate, particularly for facilitating compaction, can also be used herein.

Coated tablets additionally comprise suitable coating materials, for example, film coating agents with coating aids, especially those mentioned below. Coated tablets include, but are not limited to, sugar-coated tablets and film-coated tablets.

Powders are finely dispersed solids of formulations of the present invention with particle sizes usually of less than about 1 mm. The above statements about granules apply correspondingly.

Preference is given according to the present invention to capsules packed with granules, powders or pellets of formulations of the present invention, instant granules and granules for oral suspension composed of formulations of the present invention with addition of masking flavors, and, in particular, tablets and coated tablets.

The dosage forms of the present invention are usually packed in a suitable form. Pushout (blister) packs made of plastic and/or metal for solid dosage forms are frequently used.

The present invention also relates to a process for producing a formulation of the present invention by mixing (blending) components i), ii) and optionally iii) to form a plastic mixture. Thus, to form the plastic mixture, at least two measures are necessary, first, the mixing (blending) of the components forming the mixture, and second, the plastification thereof, i.e. the conversion thereof into the plastic state. These steps may take place for one or more components or portions of components successively, intermeshingly, alternately or in another way. Accordingly, it is possible in principle for the conversion into the plastic state to take place concurrently during a mixing process, or for the mixture first to be mixed and then to be converted into the plastic state. A plurality of plastic mixtures differing in composition may be formed during a process and are mixed together and/or with other components or portions of components. For example, a premix of a portion of the components, e.g. excipient component and/or binder component, can be formulated to form granules, and the granules can then be converted, with the addition of other components, e.g. the active substance component, into a plastic mixture whose composition may correspond to that of the formulation. It is also possible for all the components to first be combined and then either converted into the plastic state at the same time as mixing or first mixed and then converted into the plastic state.

The formation of a plastic mixture can take place by melting or, with additional input of mechanical energy, e.g. by kneading, mixing or homogenizing, below the melting point of the mixture. The plastic mixture is preferably formed at temperatures below about 220° C. The formation of the plastic mixture usually does not take place by one or more components being converted into a paste or partially dissolved with liquids or solvents, but takes place mainly or exclusively by thermal or thermal/mechanical action on the component(s), i.e. by thermal plastification. The plastic mixture is preferably formed by extrusion, more preferably, by melt extrusion. The plastification process steps can be carried out in a manner known per se, for example as described in EP-A-0 240 904, EP-A-0 337 256, EP-A-0 358 108, WO 97/15290 and WO 97/15291. The contents of these publications and, in particular, the statements about melt extrusion disclosed therein are incorporated herein by reference.

In principle, there are two possible ways by which solubilization of the active substance can be achieved during melt extrusion. First, the extrusion process is carried out at a temperature that is higher than the melting point of the active substance and high enough for plastification of the binder. In this case, the molten active substance can be solubilized in the plastified binder by means of mixing and kneading which takes place during extrusion (method A). Second, if the solubility of the active substance is good, a solubilization in the plastified binder can take place without the need to melt the active substance. This situation is comparable to the dissolution of water-soluble compounds (e.g. sugar) in water which is also possible without the need for prior melting the compound (method B). Fenofibrate is an active substance with a relatively low melting point (approximately 80° C.) and therefore, a melting of the active substance can be expected during extrusion which is carried out normally at temperatures higher than 80° C. according to method A.

Fenofibric acid has a melting point of 184° C. (*Arzneimittel-Forschung* 26, 885–909 (1976), see page 887) which is much higher than the melting point of fenofibrate. Therefore, solubilization of fenofibric acid in the binder(s) may take place according to method B. Moreover, method B could be advantageous even for processing fenofibrate in order to prevent any chemical degradation of fenofibrate at temperatures exceeding the melting point of fenofibrate.

In addition to the melt extrusion technology, there are other known technologies for embedding active substances in binders in molecular dispersed form. The most common technique uses organic solvents where both the active substance(s) and the excipients (binders) are soluble. The solution of both compounds (active substances and binder(s)) are combined and then the solvent is removed completely. This process has a number of disadvantages because it requires the use of organic solvents which causes a lot of problems during manufacturing. Although possible, this is not the preferred process according to the present invention.

In the case of low melting compounds like fenofibrate, the active substance can be placed in a beaker and heated together with the binder while the whole mixture is stirred. This technique does not use organic solvents but is based on a batch-process that requires much longer stirring and heating than in the case of a continuous process like melt extrusion. This means that the residence time of the drug at high temperature is much longer and thus increases the risk of possible degradation of both active substance(s) and binder(s). Furthermore, this process normally requires low-viscosity melts which are obtained by using e.g. PEG. Although possible, this is not the preferred process according to the present invention.

It should be possible to convert the binder component into a plastic state in the complete mixture of all the components in the temperature range from about 30 to about 200° C., preferably about 40 to about 170° C. The glass transition temperature of the mixture should therefore be below about 220° C., preferably below about 180° C. If necessary, it can be reduced by conventional, physiologically acceptable plasticizing excipients.

Examples of plasticizers include, but are not limited to, organic, preferably, involatile compounds, such as, for example, $C_7$–$C_{30}$-alkanols, ethylene glycol, propylene glycol, glycerol, trimethylolpropane, triethylene glycol, butandiols, pentanols such as pentaerythritol and hexanols, polyalkylene glycols, preferably having a molecular weight of from about 200 to about 1,000, such as, for example, polyethylene glycols (e.g. PEG 300, PEG 400), polypropylene glycols and polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters, in particular triethylcitrate), fatty acid esters such as glycerol mono-, di- or triacetate or sodium diethyl sulfosuccinate. The concentration of plasticizer is, where present, generally about 0.5 to about 30, preferably about 0.5 to about 10% by weight based on the total weight of polymer and plasticizer and from about 0.1 to about 40, especially from about 0.5 to about 20 and more specifically from about 1 to about 10% by weight based on the total weight of the extruded formulation. The plasticizer can be added during extrusion by pumping the liquid directly into the extruder. Alternatively, the plasticizer can be granulated with one or all of the other solid components of the formulation prior to extrusion.

The amount of plasticizer does not exceed about 30% by weight based on the total weight of polymer and plasticizer so that, in the area of solid forms, storage-stable formulations and dosage forms showing no cold flow are formed. Accordingly, it is preferred that the glass transition temperature of the final formulation be at least 40° C., preferably at least 50° C.

The process of the present invention can advantageously be carried out at temperatures below about 220° C. and preferably below 180° C., but above room temperature (25° C.), preferably above about 40° C. A preferred temperature range for the extrusion of formulations of the present invention is about 80° C. to about 180° C. The process is carried out in a temperature range extending to about 40° C., preferably about 30° C., and most preferably about 20° C., upward or downward from the softening point of the mixture of the components.

In certain cases, it may be beneficial to add components or portions of components as solution or suspension in a solvent. Particularly expedient ones are low molecular weight volatile solvents, e.g. water, $C_1$–$C_6$-monoalcohols and ethers thereof, esters of $C_1$–$C_6$-monoalkanols with $C_1$–$C_6$-carboxylic acids and alkanes. Another solvent that can be used is liquid $CO_2$. Water-soluble active substances can be employed as aqueous solution or, optionally, be taken up in an aqueous solution or dispersion of the binder component or a portion thereof. Corresponding statements apply to active substances which are soluble in one of the solvents mentioned, if the liquid form of the components used is based on an organic solvent. The components to be employed according to the present invention may contain small amounts of solvent, e.g. because of hygroscopicity, trapped solvent or water of crystallization. The total solvent content of the plastic mixture is preferably less than about 15%, more preferably less than about 10%, and most preferably less than about 5%. The plastic mixture is preferably formed without the addition of a solvent, i.e. in particular by solvent-free melt extrusion.

The components, i.e. active substance and/or binder and, where appropriate, other excipients, can first be mixed and then be converted into the plastic state and homogenized. This can be done by operating the apparatuses such as, but not limited to, stirred vessels, agitators, solids mixers etc. alternately. Sensitive active substances can then be mixed in (homogenized), preferably in "intensive mixers" in plastic phase with very small residence times. The active substance(s) may be employed as such, i.e. in particular in solid form, or as solution, suspension or dispersion.

The plastification, melting and/or mixing takes place in an apparatus typically used for this purpose. Extruders or heatable containers with agitator, e.g. kneaders (like those of the type mentioned hereinafter) are particularly suitable.

It is also possible to use as mixing apparatus those apparatuses that are employed for mixing in the field of plastics technology. Suitable apparatuses are described, for example, in "Mischen beim Herstellen and Verarbeiten von Kunststoffen", R. Pahl, VDl-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, particularly mixer/kneader reactors (e.g. ORP, CRP, AP, DTB from List or Reactotherm from Krauss-Maffei or Ko-Kneader from Buss), trough mixers or internal mixers or rotor/stator systems (e.g. Dispax from IKA).

The process steps of mixing and plastification, and particularly, the melting, can be carried out in the same apparatus or in two or more apparatuses operating separately from one another. The preparation of a premix can be carried out in one of the mixing apparatuses described above and normally used for granulation. Such a premix can then be fed directly into an extruder, for example, and then be extruded where appropriate with the addition of other components.

It is possible in the process of the present invention to employ as extruders single screw machines, intermeshing screw machines or else multiscrew extruders, especially twin screw extruders that are suited to produce solid dispersions of a drug dissolved or dispersed in a polymer (cf. EP 0 580 860 A), corotating or counter-rotating and, where appropriate, equipped with kneading disks. If it is necessary in the extrusion to evaporate a solvent, the extruders are generally equipped with an evaporating section. Examples of extruders which can be used include, but are not limited to, those of the ZSK series from Werner & Pfleiderer.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly preferred if the viscosities and pressures are high. Liquid media can be metered in by a suitable pump unit.

The mixture that has been obtained by mixing and converting the polymer component, the active substance component and, where appropriate, other excipients into the plastic state is pasty, of high viscosity or low viscosity (thermoplastic) and can therefore also be extruded. The glass transition temperature of the mixture is preferably below the decomposition temperature of all the components present in the mixture.

The formulation of the present invention is suitable as a plastic mixture, where appropriate after cooling or solidification, preferably as extrudate, for all conventional processes for manufacturing conventional oral dosage forms, in particular drug forms.

The present invention also relates to a process for producing dosage forms based on formulations of the present invention as described herein. Thus, the formulation can be produced by the above process and can be converted into the required dosage form where appropriate with the addition of other excipients. This can be done using shaping process measures such as by shaping the plastic mixture, such as by extrusion or melt extrusion, and shaping the plastic mixture, particularly, the extrudate, where appropriate after cooling or solidification, for example by granulation, grinding, compression, casting, injection molding, tableting under pressure, tableting under pressure with heat. It is also possible to convert a formulation into a desired dosage form by introducing it into suitable vehicles. It is also possible to process solid formulations into semisolid or liquid formulations through the addition of suitable vehicles.

A large number of solid dosage forms can be manufactured in this way. For example, powders or granules can be produced by grinding or chopping the solidified or at least partly solidified plastic mixture, and can be either used directly for treatment or, where appropriate, with the addition of conventional excipients, further processed to the above dosage, in particular drug forms, especially tablets.

Dosage forms are preferably shaped before solidification of the plastic mixture and result in a form that can be employed for treatment where appropriate after coating in a conventional way.

The shaping to the dosage form before solidification can take place in a variety of ways depending on the viscosity of the plastic mixture, for example, by casting, injection molding, compression, or calendering. This is done by conveying the plastic mixture described above in the process according to the present invention to one or more shaping steps. The conveying can take place by pressing, pumping, e.g. with gear pumps, or, preferably, with an extruder.

The plastic mixture can be formed in one or more, preferably one, extruder and conveyed by the latter or a downstream extruder to the shaping steps. It has proved to be advantageous in many cases to extrude on a downward incline and/or where appropriate to provide a guide channel for transporting the extrudate in order to ensure safe transport and prevent rupture of the extrudate.

It may also be advantageous, depending on the number and compatibility of the active substances to be employed, to employ multilayer extrudates, for example coextrudates, as described in WO 96/19963, in the process of the present invention.

Multilayer solid dosage forms can be produced by coextrusion, in which case a plurality of mixtures of one or more of the components described above are conveyed together into an extrusion die so that the required layer structure results. Different binders are preferably used for different layers.

Multilayer dosage forms can comprise two or three layers. They may be in open or closed form, particularly as open or closed multilayer tablets.

If the shaping takes place by coextrusion, the mixtures from the individual extruders or other units are fed into a common coextrusion die and extruded. The shape of the coextrusion dies depends on the required dosage form. Examples of suitable dies are those with a flat orifice, called slit dies, and dies with an annular orifice cross section. The design of the die depends on the formulation base used and, the binder component and the desired dosage form.

The first shaping step takes place when the extrudate emerges from the extruder through suitably shaped dies, draw plates or other orifices, for example, through a breaker plate, a circular die or a slit die. This usually results in a continuous extrudate, particularly with a constant cross section, for example in the form of a ribbon or of a strand, preferably with a circular, oval, rounded or flat and broad cross section.

Suitable downstream shaping steps for extrudates are, for example, cold cut, that is to say, the cutting or chopping of the extrudate after at least partial solidification, hot cut, that is, the cutting or chopping of the extrudate while still in the plastic form, or pinching off the still plastic extrudate in a nip device. It is possible with hot or cold cut to obtain, for example, granules (hot or cold granulation) or pellets. Hot granulation usually leads to dosage forms (pellets) with a diameter of from about 0.5 to about 3 mm, while cold granulation normally leads to cylindrical products with a length to diameter ratio of from about 1 to about 10 and a diameter of from about 0.5 to about 10 mm. It is possible in this way to produce monolayer but also, on use of coextrusion, open or closed multilayer dosage forms, for example oblong tablets, pastilles and pellets. The dosage forms can be provided with a coating by conventional methods in a downstream process step. Suitable materials for film coatings are the polymers mentioned as enteric binders. Further shaping steps may also follow, such as, for example, rounding off the pellets obtained by hot or cold cut using rounding-off devices as described in DE-A-196 29 753.

It is particularly preferred for all of the shaping steps to be carried out on the still plastic mixture or still plastic extrudate. Besides hot cut, where appropriate with subsequent rounding off, a suitable process is one in which the plastic mixture is shaped to the dosage form in a molding calender. This is done by conveying a still plastic mixture or a still plastic extrudate to a suitable molding calendar. Suitable molding calenders usually have molding rolls and/or belts for the shaping, with at least one of the molding rolls and/or at least one of the belts having depressions to receive and shape the plastic mixture. It is preferred to use a molding calender with counter-rotating molding rolls, with at least one of the molding rolls having on its surface depressions to receive and shape the plastic mixture. Suitable molding calenders and devices containing molding rolls are generally disclosed for example in EP-A-0 240 904, EP-A-0 240 906 and WO 96/19962, and suitable belts and devices containing belts are generally disclosed for example in EP A-0 358 105, which are expressly incorporated herein by reference.

The shaping of the still plastic mixture or still plastic extrudate preferably takes place at melt temperatures below about 220° C., more preferably below about 180° C. and most preferably below about 150° C., such as, for example, in the temperature ranges necessary to form the plastic mixture or at lower temperatures. If the shaping takes place at lower temperatures, it can take place at from about 5 to about 70° C., preferably about 10 to about 50° C. and most preferably about 15 to about 40° C. below the highest temperature reached on formation of the plastic mixture, but preferably above the solidification temperature of the plastic mixture.

Preference is given to formulations and dosage forms obtainable by one of the processes described above.

The formulations of the present invention, when used as a dosage form and thus providing an effective amount of active substance, are administered to the individual to be treated, including a human, domestic or agricultural animals. Whether such a treatment is indicated and what form it is to take depends on the individual case and may be subject to medical assessment (diagnosis) which includes the signs, symptoms and/or dysfunctions which are present, the risks of developing certain signs, symptoms and/or dysfunctions, and other factors. The formulations of the present invention are ordinarily administered together or alternately with other products in such a way that an individual to be treated receives a daily dose of about 50 mg to about 250 mg fenofibrate on oral administration.

The formulations and dosage forms of the present invention are mainly used in pharmacy, for example in the pharmaceutical sector as lipid regulating agents.

2. Novel Salts of Fenofibric Acid

In another aspect, the present invention relates to novel salts of fenofibric acid. In one embodiment, these novel salts are selected from the group consisting of choline, ethanolamine, diethanolamine, piperazine, calcium and tromethamine. The structure of each of these salts is provided in Example 27, Table 3.

The novel salts of the present invention are base addition salts that can be prepared by combining fenofibric acid and a base in a suitable solvent system and then mixing at an appropriate temperature. The determination of a suitable solvent system and appropriate temperature for preparing such salts can be readily determined by one of ordinary skill in the art. By way of example and not of limitation, Table 1 below shows examples of bases and solvents that can be used to make the novel salts of the present invention.

TABLE 1

| Base | Solvent | Salt |
|---|---|---|
| Choline Hydroxide or Choline Chloride | Isopropanol, Methanol | Choline |
| Diethanolamine | Isopropanol | Diethanolamine |
| Tris(hydroxymethyl)aminomethane (common name Tromethamine) | Isopropanol, Water | Tromethamine |
| Calcium Carbonate, Calcium Hydroxide or Calcium Chloride | Isopropanol, Water | Calcium (2:1) |
| Ethanolamine | Ethyl acetate | Ethanolamine |
| Piperazine | Isopropanol, Water | Piperazine(2:1) |

The inventors of the present invention have discovered that the novel salts of the present invention, namely, choline, ethanolamine, diethanolamine, piperazine, calcium and tromethamine, exhibit the desirable characteristic of photostability. The terms "photostability" and "photostable" are used interchangeably herein and refer to a lack of degradation induced by exposure to light from 300–800 nm under the conditions described in the "Guideline for the Photostability Testing of New Drug Substances and Products" (International Conference on Harmonization. *Federal Register* 1997; 65(95):27115–22, which is herein incorporated by reference) (hereinafter referred to as the "Guidelines"). As used herein, the term of "lack of degradation" means a recovery of 95% or greater on average, preferably a recovery of 97% or greater on average and most preferably, a recovery of 99% or greater on average of the novel salts of the present invention after exposure to light from 300–800 nm under the conditions described in the Guidelines described above and pursuant to the assay described in Example 28. The inventors of the present invention expect the novel salts of the present invention to exhibit photostability under less rigorous light conditions (exposures) and recognize that the novel salts may not exhibit photostability under more rigorous light conditions (exposures) than those described herein and in Example 28.

The finding that the novel salts of the present invention are photostable was unexpected. Specifically, the inventors of the present invention discovered that the photostability of fenofibric acid and salts of fenofibric acid is unpredictable. More specifically, although the inventors of the present invention discovered that the novel salts of the present invention are photostable, the inventors found that certain forms of fenofibric acid as well as other salts of fenofibric acid (such as L-lysine and meglumine, which are discussed in more detail in the Examples) are not photostable. With respect to fenofibric acid, the inventors of the present invention found one form of fenofibric acid that is commercially available is photostable while another commercially available form of fenofibric acid is not photostable.

Because the novel salts of the present invention are photostable, it is believed these salts and pharmaceutical formulations containing these salts will not exhibit unacceptable degradation or change (such as a change in the physicochemical properties of the salts) when exposed to light. The inventors recognize, however, that pharmaceutical formulations containing said novel salts may contain one or more pharmaceutically acceptable carriers or excipients or other ingredients that are photolabile even though the salts described herein (which would be the active pharmaceutical ingredient), are photostable.

The photostability of the novel salts of the present invention facilitates their manufacturability and the manufacturability of pharmaceutical formulations containing these salts. Additionally, because the novel salts of the present invention are photostable, no special light-protected facility, storage or packing of these salts or pharmaceutical formulations should be required, provided that said formulations do not contain one or more other ingredients that are photolabile.

As described in detail in the Examples, certain characterization and performance data, were examined for each of the above-described novel salts of the present invention. This data is summarized below in Table 2.

TABLE 2

Novel Salts of Fenofibric Acid

| Salt | Melting Point Range (° C.) | PLM[1] |
|---|---|---|
| Choline | 209–211 | Crystalline |
| Diethanolamine | 142–144 | Crystalline |
| Tromethamine | 198–204 | Crystalline |
| Calcium (2:1) | 242–246* | Crystalline |
| Ethanolamine | 121–123 | Crystalline |
| Piperazine (2:1) | 215–217 | Crystalline |

*Melting point of solid after dehydration and recrystallization peaks
[1]Polarized Light Microscopy In a second embodiment, the present invention relates to pharmaceutical formulations in a form of a molecular dispersion that comprise one or more of the novel salts of the present invention. The pharmaceutical formulations can be formulations such as those described under heading 1 herein and contain one or more of the novel salts of the present invention and at least one enteric binder.

By way of example, and not of limitation, examples of the present invention will now be given.

EXAMPLE 1

Fenofibrate (120 g corresponding to 15% w/w) and HP 55 S (hydropropylmethylcellulose phthalate, ShinEtsu, 672 g corresponding to 84% w/w) and colloidal silica (Aerosil 200, 8 g corresponding to 1% w/w) were blended for 4 minutes in a turbula blender. The powder mixture was then extruded in a twinscrew extruder (screw diameter 18 mm) with an feeding of 1.0 kg/h at a temperature of the melt at 165° C. A clear, transparent melt rope with a thickness of approximately 1.0 cm was extruded. This material was directly formed into tablets (oblong-shaped) by calendering between two co-rotating rollers. By this process clear, transparent tablets of high hardness were obtained having a tablet weight of approximately 550 mg.

EXAMPLE 2

The tablets according to Example 1 were milled in laboratory mill and the resulting powder was analyzed by DSC between 20 and 250° C. (Mettler Toledo DSC-820; 8.45 mg in a closed pan at 10 K/min). No endothermic melting peaks were observed, indicating that the fenofibrate was present in the polymer matrix in non-crystalline form.

EXAMPLE 3

The powder deriving from milling of the tablets according to Example 2 was analyzed by WAXS (wide angle x-ray scattering; Bruker AXS D-5005). There were no distinct peaks visible in the WAXS indicating that no crystalline fenofibrate was present in the formulation.

EXAMPLE 4

The tablets according to Example 1 were analyzed with respect to possible drug degradation by HPLC according to the method described in Eur. pharm. for fenobibratum. The amount of the two known impurities according to USP were as follows: Impurity A=0.067%, Impurity B=0.071%. Although the extrusion was performed at a temperature far higher (165° C.) than the melting point of fenofibrate (approximately 80° C.) degradation took place to a very minor amount only.

EXAMPLE 5

Drug dissolution from the tablets according to Example 1 was measured according to the USP paddle method at 37° C. in 900 ml aqueous solution of sodium dodecylsulfate (SDS, 0.05 mol/l) with a rotation speed of 75 rpm. Dissolution of the fenofibrate from the tablets was extremely slow in this medium. Only about 1% of the fenofibrate was liberated even after 90 minutes.

EXAMPLE 6

The milled tablet material according to Example 2 was screened (63<x<500 microns). Hard gelatin capsules (size 00, mean total capsule weight 740 mg) were filled with a powder mixture containing the screened material (555 mg/capsule) together with mannitol (75 mg/capsule) and Aerosil 200 (5.55 mg/capsule). These capsules contained 83.25 mg fenofibrate.

EXAMPLE 7

Drug dissolution from the capsules according to Example 6 was analyzed by the USP paddle method according to example 5 in 0.05 mol/l SDS solution. Fenofibrate release was shown to be faster compared to the unmilled tablets but was again relatively slow (16% dissolution after 90 minutes).

EXAMPLE 8

Drug dissolution from the capsules according to Example 6 was analyzed by the USP paddle method at 37° C. in 900 ml phosphate buffer (pH 6.8) additionally containing sodium dodecylsulfate (SDS, 0.05 mol/1) with a rotation speed of 75 rpm. At this pH the dissolution was significantly faster compared to the unbuffered aqueous medium (91% dissolution after 90 minutes).

EXAMPLE 9

Dissolution analysis was performed according to Example 8, but with a phosphate buffer having a pH of 7.2 together with 0.05 20 mol/l SDS. Drug dissolution was nearly 100% after 90 minutes.

EXAMPLE 10

The capsules according to Example 6 were tested with respect to bioavailability in a dog model (n=4 dogs were used in this study, fasted). The marketed product (Tricor capsules, 67 mg fenofibrate/capsule) was used as reference. Plasma concentrations of fenofibric acid were determined by HPLC-MS. The results showed a remarkable increase in bioavailability for the formulation according to the present invention (approximately 4-fold increase in AUC) compared to the Tricor capsules.

EXAMPLE 11

Fenofibrate (150 g corresponding to 15% w/w) and HP 50 (hydroxypropylmethylcellulose phthalate, ShinEtsu, 215 g corresponding to 21.5% w/w) and PVP (Kollidon K25, BASF, 625 g corresponding to 62.5% w/s) and colloidal silica (Aerosil 200, 10 g corresponding to 1% w/w) were blended for 4 minutes in a turbula blender. The powder mixture was then extruded in a twin-screw extruder (screw diameter 18 mm) with a feeding of 1.4 kg/h at a temperature of the melt at 149° C. A clear, transparent melt rope with a thickness of approximately 1.0 cm was extruded. This material was directly formed into tablets (oblong-shaped) by calendering between two co-rotating rollers. By this process opaque, translucent tablets of high hardness were obtained having a tablet weight of approximately 550 mg.

EXAMPLE 12

Fenofibrate (150 g corresponding to 15% w/w) and HP 50 (hydroxpropylntethylcellulose phthalate, ShinEtsu, 190 g corresponding to 19% w/w), PVP (Kollidon K25, BASF, 600 g corresponding to 60% w/w) and polyoxyethylated oleic glyceride (Labrafil M 1944 CS, Gattefosse, 50 g corresponding to 5% w/w) and colloidal silica (Aerosil 200, 10 g corresponding 1% w/w) were blended for 4 minutes in a turbula blender. The liquid compound (Labrafil M 1944 CS) was granulated with the PVP prior to extrusion. The powder mixture including all ingredients was then extruded in a twin-screw extruder (screw diameter 18 mm) with a feeding rate of 2.0 kg/h at a temperature of the melt at 145° C. A clear, transparent melt rope with a thickness of approximately 1.0 cm was extruded. This material was directly formed into tablets (oblong-shaped) by calendering between two co-rotating rollers. By this process opaque, translucent tablets of high hardness were obtained having a tablet weight of approximately 550 mg.

EXAMPLE 13

Fenofibric acid (120 g corresponding to 15% w/w) and HP 55 (hydroxypropylmethylcellulose phthalate, ShinEtsu, 672 g corresponding to 85% w/w) and colloidal silica (Aerosil 200, 8 g corresponding to 1% w/w) were blended and extruded as outlined in Example 1. A clear drug-containing melt was obtained. Transparent tablets with high hardness were obtained having a tablet weight of approximately 550 mg (corresponding to 82.5 mg fenofibric acid per tablet).

EXAMPLE 14

The crystallinity of the drug in the melt-extruded samples of Example 13 were analyzed with respect to DSC and WAXS according to Examples 2 and 3. No crystalline drug material was detected neither by DSC nor by WAXS.

EXAMPLE 15

Hard gelatin capsules were prepared according to example 6 containing milled extrudate (63<x<500 microns) of the melt-extrudate of Example 13. These capsules contained 73.79 mg fenofibric acid (mean) corresponding to 83.53 mg fenofibrate (f=1.132), 413.23 mg HP 66 (mean), 134.63 mg mannitol (mean) and 11.57 mg Aerosil 200 (mean). The total weight of these capsules was 747.1 mg (mean).

EXAMPLE 16

The bioavailability o f the capsule formulation according to Example 15 (containing fenofibric acid) was tested with respect to bioavailability in the dog model in comparison to the capsule formulation according to example 6 (which contains fenofibrate). The bioavailability of the fenofibric acid-containing capsule (according to Example 15) was shown to be twice as high as in the case of the fenofibrate-containing capsule formulation (according to Example 6).

EXAMPLE 17A

Method for Making Choline Salt

Fenofibric acid (10.0 g, 0.0314 mol) was suspended in 100 mL isopropanol and the mixture heated to 65° C. A solution of choline hydroxide in methanol (8.58 g, 45 wt %, 0.0319 mol) was diluted with 20 mL isopropanol and approximately two thirds of the solution was added to the fenofibric acid suspension. Optionally, seed crystals of the choline salt can be added to expedite the formation of crystals. The remaining one third of the choline hydroxide solution was added followed by a 15 mL rinse of the addition funnel with isopropanol. The product crystallized out of solution and the slurry was mixed at 65° C. for 0.5 hour, cooled to 20° C. over 5 hours, and then mixed at 20° C. overnight. The product was filtered off and rinsed with 30 mL of isopropanol. The solid was dried in a vacuum oven at 35° C. with a nitrogen purge for approximately 24 hours. The dry weight of solid was 11.83 g, or 89.4% yield. $^1$H NMR (400 MHz, D$_2$O) δ 7.75 (m, 2H), 7.70 (m, 2H), 7.55 (m, 2H), 6.93 (m, 2H), 4.03 (m, 2H), 3.49 (m, 2H), 3.17 (s, 9H), 1.59 (s, 6H); Anal. Calcd. for $C_{22}H_{28}ClNO_5$: C, 62.63; H, 6.69; N, 3.32; Cl, 8.40. Found: C, 62.70; H, 7.12; N, 3.36; Cl, 8.23.

EXAMPLE 17B

Alternate Method for Making Choline Salt

Fenofibric acid (10.0 g, 0.0314 mol) and sodium bicarbonate (2.64 g, 0.0314 mol) were suspended in 75 mL of methanol and the mixture heated to 55° C. to dissolve the solids. A solution of choline chloride (4.40 g, 0.0315 mol) in 15 mL of methanol was added. The solution was filtered to remove the precipitated sodium chloride, and the filter rinsed with 20 mL of methanol. The filtrate was diluted with 40 mL of isopropanol and concentrated to a volume of approximately 120 mL. The solution was filtered and the filter rinsed with 20 mL of isopropanol. The filtrate was concentrated to a solid residue weighing 14 g. The residue was suspended in 70 mL of isopropanol and heated to 55° C. for 0.5 hour, cooled to 22° C. over 5 hours, and mixed at 22° C. for approximately 16 hours. The product was filtered off and rinsed with 35 mL of isopropanol. The solid was dried in a vacuum oven at 50° C. with a nitrogen purge for 5 hours. The dry weight of solid was 12.98 g, or 98.1% yield.

EXAMPLE 18A

Method for Making Tromethamine Salt

Fenofibric acid (10.0 g, 0.0314 mol) and tris(hydroxymethyl)aminomethane (or tromethamine) (3.8 g, 0.031 mol) were suspended in 120 mL isopropanol and the mixture heated to 65° C. The product crystallized out of solution. The slurry was mixed at 65° C. for 1.0 hour, cooled to 20° C. over 5 hours, and then mixed at 20° C. for 0.5 hour. The product was filtered off and rinsed with 25 mL of isopropanol. The solid was dried in a vacuum oven at 35° C. with a nitrogen purge for approximately 20 hours. The dry weight of solid was 13.66 g, or 99.0% yield. $^1$H NMR (400 MHz, CD$_3$OD) δ 7.69 (m, 2H), 7.68 (m, 2H), 7.53 (m, 2H), 6.95 (m, 2H), 3.69 (s, 6H), 1.59 (s, 6H); Anal. Calcd. for $C_{21}H_{26}ClNO_7$: C, 57.34; H, 5.96; N, 3.18; Cl, 8.06. Found: C, 57.15; H, 5.97; N, 3.06; Cl, 8.07.

EXAMPLE 18B

Alternate Method for Making Tromethamine Salt

Fenofibrate (33.0 g, 0.0914 mol) was suspended in 33 mL of isopropanol and aqueous NaOH was added (64.9 g of a 8.47% solution, 5.50 g NaOH, 0.138 mol, 1.5 eq). The mixture was heated to reflux for 2.75 h, and then cooled to approximately 35° C. The solution was diluted with 46 g of water, and then a solution of tromethamine (12.2 g, 0.101 mol, 1.1 eq) in 33 g of water was added. A solution of hydrochloric acid (52.0 g of a 10.3% solution, 5.34 g of HCl, 0.146 mol, 1.6 eq) was added and the product crystallized from solution. The slurry was heated to 50° C. for 1 h, cooled to 22° C. over 3 h, and mixed at 22° C. approximately 16 h. The product was filtered and rinsed with 100 g of water. The product was dried in a vacuum oven at 50° C. with a nitrogen purge to a constant weight. The dry weight was 40.23 g, or 96.4% yield.

EXAMPLE 19A

Method for Making Calcium Salt

Fenofibric acid (550.3 g, 1.726 mol) was suspended in 1.5 kg of water. An aqueous NaOH solution was added (137.2 g of a 50.5% solution, 69.29 g NaOH, 1.732 mol, 1.0 eq.), and the addition funnel rinsed with 50 g of water. The solution was filtered, the transfer aided with a 400 g rinse of water, and the filtrate heated to 70° C. An aqueous solution of calcium chloride (126.9 g of calcium chloride dihydrate in 300 g of water, 0.8631 mol, 0.5 eq) was added over 30 minutes, and the addition funnel rinsed with 60 g of water. The product crystallized out of solution during the addition of calcium chloride. The slurry was diluted with 5.3 kg of water and 2 L of isopropanol and mixed for approximately 1 h at 50° C., cooled to 22° C. and mixed overnight. The slurry was diluted with 800 g of water and 800 mL of isopropanol, and the product was then filtered and rinsed with 2.5 kg of water, and 750 mL of isopropanol. The solid was dried in a vacuum oven at 60° C. with a nitrogen purge for approximately 60 h. The weight of solid after drying was 602.6 g, with 4.3 weight % of water by Karl Fischer analysis. Adjusting for the water content the yield was 98.9%. $^1$H NMR (400 MHz, CD$_3$OD) δ 7.68 (m, 8H), 7.50 (m, 4H), 6.96 (m, 4H), 1.60 (s, 12H); Anal. Calcd. for C$_{34}$H$_{28}$CaCl$_2$O: C, 60.45; H, 4.18; Cl, 10.50. Found: C, 59.91; H, 4.1 1; Cl, 10.65.

EXAMPLE 19B

Alternate Method for Making Calcium Salt

Fenofibric acid (4.0 g, 0.013 mol) was suspended in 100 mL isopropanol and the mixture heated to 45° C. A suspension of calcium carbonate (0.628 g, 0.00627 mol) in 40 mL water was added, rinsing the addition funnel with 10 mL of water. The mixture was heated to 60° C. and then cooled to 45° C. and the product crystallized out of solution. The mixture was heated to 65° C., cooled to 22° C. over 2.5 hours, and then mixed at 22° C. for 1 hour. The product was filtered off and rinsed with 30 mL of isopropanol. The solid was dried in a vacuum oven at 40° C. with a nitrogen purge for approximately 20 hours, and then at 80° C. for 3 hours. The dry weight of solid was 3.87 g, with 3.2 weight % of water by Karl Fischer analysis. Adjusting for the water content the yield was 88.4%.

EXAMPLE 20

Method of Making Diethanolamine Salt

Fenofibric acid (10.0 g, 0.0314 mol) was suspended in 100 mL of isopropanol and the mixture heated to 65° C. A solution of diethanolamine (3.3 g, 0.031 mol) in 20 mL isopropanol was prepared and approximately two thirds of the solution was added to the fenofibric acid suspension. Optionally, seed crystals of the diethanolamine salt may be added to expedite the formation of crystals. The remaining one third of the diethanolamine solution was added with a 15 mL rinse of the addition funnel with isopropanol. The mixture was cooled to 50° C. and product crystallized out of solution. The slurry was heated to 65° C. and mixed for 0.5 hour, cooled to 20° C. over 5 hours, and then mixed at 20° C. for 1 hour. The product was filtered off and rinsed with 30 mL of isopropanol. The solid was dried in a vacuum oven at 35° C. with a nitrogen purge for approximately 24 hours. The dry weight of solid was 12.22 g or 91.9% yield. $^1$H NMR (400 MHz, D$_2$O) δ 7.74 (m, 2H), 7.69 (m, 2H), 7.54 (m, 2H), 6.92 (m, 2H), 3.84 (m, 4H), 3.22 (m, 4H), 1.59 (s, 6H); Anal. Calcd. for C$_{21}$H$_{26}$ClNO$_6$: C, 59.50; H, 6.18; N, 3.30; Cl, 8.36. Found: C, 59.36; H, 6.42; N, 3.18; Cl, 8.38.

EXAMPLE 21

Method of Making L-Lysine Salt

Fenofibric acid (10.0 g, 0.0314 mol) and L-Lysine (4.60 g, 0.0315 mol) were suspended in 125 mL of ethanol. The mixture was heated to 65° C. Optionally, seed crystals of the L-lysine salt can be added to expedite the formation of crystals. The mixture slowly cooled to 22° C. While mixing at 22° C. overnight, the product crystallized out of solution. The slurry was heated to 50° C. for 1 hour and then cooled to 22° C. The product was filtered off and rinsed with 35 mL of ethanol. The solid was dried in a vacuum oven at 40° C. with a nitrogen purge for approximately 20 hours. The dry weight of solid was 12.24 g, or 83.9% yield. $^1$H NMR (400 MHz, D$_2$O) δ 7.73 (m, 2H), 7.68 (m, 2H), 7.53 (m, 2H), 6.92 (m, 2H), 3.71 (t, J=6.1, 1H), 2.99 (m, 2H), 1.87 (m, 2H), 1.69 (m, 2H), 1.58 (s, 6H), 1.44 (m, 2H); Anal. Calcd. for C$_{23}$H$_{29}$ClN$_2$O$_6$: C, 59.42; H, 6.29; N, 6.03; Cl, 7.63. Found: C, 59.26; H, 6.32; N, 6.11; Cl, 7.70.

EXAMPLE 22A

Method of Making Piperazine Salt

Fenofibric acid (10.0 g, 0.0314 mol) was suspended in 100 mL of isopropanol and the mixture heated to 65° C. A solution of piperazine (1.4 g, 0.016 mol) in 20 mL isopropanol was prepared with heating and added to the fenofibric acid suspension, with a 10 mL rinse of the addition funnel with isopropanol. The product crystallized during addition of the piperazine solution. The slurry was mixed at 65° C. for 0.8 hours, cooled to 20° C. over 4 hours, and then mixed at 20° C. for 1.5 hours. The product was filtered off and rinsed with 30 mL of isopropanol. The solid was dried in a vacuum oven at 40° C. with a nitrogen purge for approximately 20 hours. The dry weight of solid was 11.00 g or 96.9% yield. $^1$H NMR (400 MHz, CD$_3$OD) δ 7.70 (m, 8H), 7.53 (m, 4H), 6.95 (m, 4H), 3.12 (s, 8H), 1.62 (s, 12H); Anal. Calcd. for C$_{38}$H$_{40}$Cl$_2$N$_2$O$_8$: C, 63.07; H, 5.57; N, 3.87; Cl, 9.80. Found: C, 63.01; H, 5.53; N, 3.79; Cl, 9.78.

EXAMPLE 22B

Alternate Method for Making Piperazine Salt

Fenofibrate (33.0 g, 0.0914 mol) was suspended in 33 mL of isopropanol and aqueous NaOH was added (64.9 g of a 8.47% solution, 5.50 g NaOH, 0.138 mol, 1.5 eq). The mixture was heated to reflux for 4 h, and then cooled to approximately 35° C. The solution was diluted with 46 g of water, and then a solution of piperazine (4.3 g, 0.050 mol, 1.1 eq) in 33 g of water was added. A solution of hydrochloric acid (53.1 g of a 10% solution, 5.31 g of HCl, 0.146 mol, 1.6 eq) was added and the product crystallized from solution. The slurry was heated to 50° C. for 1 h, cooled to 22° C. over 3 h, and mixed at 22° C. approximately 16 h. The product was filtered and rinsed with 100 g of water. The product was dried in a vacuum oven at 50° C. with a nitrogen purge for approximately 16 hours. The dry weight was 33.0 g, or 99.7% yield from fenofibrate.

EXAMPLE 23

Method for Making Ethanolamine Salt

Fenofibric acid (10.0 g, 0.0314 mol) was suspended in 100 mL of ethyl acetate. A mixture of ethanolamine (1.97 g, 0.323 mol) in 15 mL of ethyl acetate was added, rinsing with 10 mL of ethyl acetate. Optionally, seed crystals of the ethanolamine salt can be added to expedite the formation of crystals. The product crystallized out of solution. The slurry was heated to 50° C. for 0.3 hour, cooled to 20° C. over 1.5 hours, and then mixed at 20° C. for 1 hour. The product was filtered off and rinsed with 50 mL of ethyl acetate. The solid was dried in a vacuum oven at 40° C. with a nitrogen purge for approximately 4 hours. The dry weight of solid was 11.70 g, or 98.2% yield. $^1$H NMR (400 MHz, $D_2O$) δ 7.75 (m, 2H), 7.71 (m, 2H), 7.55 (m, 2H), 6.93 (m, 2H), 3.79 (m, 2H), 3.11 (m, 2H), 1.59 (s, 6H); Anal. Calcd. for $C_{19}H_{22}ClNO_5$: C, 60.08; H, 5.84; N, 3.69; Cl, 9.33. Found: C, 59.85; H, 6.03; N, 3.62; Cl, 9.30.

EXAMPLE 24

Method for Making Meglumine Salt

Fenofibric acid (10.0 g, 0.0314 mol) and N-methyl-D-glucamine (or meglumine) (6.12 g, 0.0313 mol) were suspended in 125 mL of ethyl acetate. The mixture was heated to 50° C., and 30 mL ethanol was added. Optionally, seed crystals of the meglumine salt can be added to expedite the formation of crystals. The solution was heated to 65° C. and then cooled to 22° C. The solution was diluted with 30 mL of heptane, heated to 55° C. and cooled slowly to 22° C. While mixing at 22° C. overnight the product crystallized out of solution. The product was filtered off and rinsed with a mixture of 30 mL of ethyl acetate, 5 mL of ethanol and 5 mL of heptane. The solid was dried in a vacuum oven at 40° C. with a nitrogen purge for approximately 4 hours. The dry weight of solid was 14.72 g, or 91.3% yield. $^1$H NMR (400 MHz, $D_2O$) δ 7.69 (m, 2H), 7.64 (m, 2H), 7.50 (m, 2H), 6.90 (m, 2H), 4.07 (m, 1H), 3.79 (m, 2H), 3.74 (m, 1H), 3.62 (m, 2H), 3.18 (m, 2H), 2.74 (s, 3H), 1.58 (s, 6H); Anal. Calcd. for $C_{24}H_{32}ClNO_9$: C, 56.08; H, 6.28; N, 2.73; Cl, 6.90. Found: C, 55.81; H, 6.26; N, 2.69; Cl, 6.85.

EXAMPLE 25

Method of Making Sodium Salt

Fenofibric acid (4.0 g, 0.013 mol) was suspended in 40 mL of isopropanol and the mixture heated to 65° C. A solution of sodium hydroxide (0.97 g, 50.7 wt %, 0.012 mol) in water was added, rinsing with 1 mL of water. The mixture was diluted with a total of 180 mL of isopropanol and concentrated by vacuum distillation to a volume of 60 mL. The product crystallized out of solution and the mixture was heated to 65° C. and diluted with 40 mL of isopropanol. The slurry was mixed at 65° C. for 0.5 hour, and then cooled to 22° C. The product was filtered off and rinsed with 80 mL of isopropanol. The solid was dried in a vacuum oven at 80° C. with a nitrogen purge for approximately 1.5 hours. The dry weight of solid was approximately 2 g, or 50% yield. $^1$H NMR (400 MHz, $D_2O$) δ 7.67 (m, 2H), 7.62 (m, 2H), 7.49 (m, 2H), 6.89 (m, 2H), 1.57 (s, 6H); Anal. Calcd. for $C_{17}H_{14}ClNaO_4$: C, 59.92; H, 4.14; Cl, 10.40. Found: C, 59.67; H, 4.15; Cl, 10.48.

EXAMPLE 26A

Method for Making Fenofibric Acid Form I

Fenofibrate (350. g, 0.970 mol) was suspended in 2 L of isopropanol. A solution of NaOH (77.6 g NaOH, 1.94 mol, 2 eq) in 1.8 L of water was added and the mixture heated to reflux for 2.7 hours. The solution was cooled to approximately 4° C. A solution of hydrochloric acid (697.2 g of a 10.03% solution, 69.90 g of HCl, 1.917 mol, 2 eq) was added maintaining the temperature at less than 5° C., and the product crystallized from solution. The crystallization can be optionally seeded with Form I fenofibric acid after approximately 50% of the hydrochloric acid is added. The slurry was warmed to 20° C. and mixed for 0.8 hours. The product was filtered, rinsed with 600 mL of 2:1 water: isopropanol, and then rinsed with 300 mL of water. The product was dried in a vacuum oven at 40° C. with a nitrogen purge for 14 hours, and then dried at 60° C. for 24 hours. The dry weight was 300.6 g, or 97.2% yield. $^1$H NMR (400 MHz, $CD_3OD$) δ 7.72 (m, 2H), 7.71 (m, 2H), 7.52 (m, 2H), 6.95 (m, 2H), 1.66 (s, 6H); Anal. Calcd. for $C_{17}H_{15}ClO_4$: C, 64.06; H, 4.74; N, Cl, 11.12. Found: C, 63.94; H, 4.64; Cl, 11.13.

EXAMPLE 26B

Method for Making Fenofibric Acid Form II

Fenofibrate (200.0 g, 0.5543 mol) was suspended in 900 mL of isopropanol. A solution of NaOH (33.0 g NaOH, 0.825 mol, 1.49 eq) in 400 mL of water was added and the mixture heated to reflux for 2 hours. The solution was cooled to approximately 75° C. A solution of hydrochloric acid (652 g of a 5.0% solution, 32.8 g of HCl, 0.894 mol, 1.6 eq) was added maintaining the temperature above 55° C., and the product crystallized from solution. The slurry was cooled to 28° C. over 3.5 hours. The product was filtered and rinsed twice with 500 mL of water. The product was dried in a vacuum oven at 60° C. with a nitrogen purge for approximately 16 hours. The dry weight was 170.7 g, or 96.6% yield.

EXAMPLE 27

Characterization of the Salts of Fenofibric Acid

Choline, diethanolamine, tromethamine, sodium, calcium, ethanolamine, meglumine, L-lysine and piperazine salts were prepared as described in Examples 17–25. Fenofibric acid form I was made as described in Example 26A and can be purchased from Labo Test, Niederschoena, Germany. Fenofibric acid form II was obtained from Synkem, Chenove Cedex, France and can be made as described in Example 26B and can also be made pursuant to U.S. Pat. No. 4,072,705, which is hereby incorporated by reference.

The melting point was determined using differential scanning calorimetry (either Model 2920 or Q1000 differential scanning calorimeter, TA Instruments, New Castle, Del.). Approximately 1–3 mg of material was placed in an aluminum pan. The sample was heated at 10° C./minute. The melting point range was determined from the DSC thermogram as the extrapolated onset temperature to the peak temperature. Tables 3 below lists the structures and molecular weight of each of the choline, diethanolamine, tromethamine, sodium, calcium, ethanolamine, meglumine, L-lysine, and piperazine.

The crystallinity of the compounds was confirmed by polarized light microscopy. The polarized light microscopy was determined using the procedures outlined in the USP, Volume 25, Chapter 776, published by the United States Pharmacopeia (2002). Table 4 below lists the melting point and crystallinity for choline, diethanolamine, tromethamine, sodium, calcium, ethanolamine, meglumine, L-lysine, and piperazine as well as for fenofibric acid forms I and II.

TABLE 3

| Salt | Salt Structure | M.W. |
|---|---|---|
| Choline | | 421.91 |
| Diethanolamine | | 423.89 |
| Tromethamine | | 439.89 |
| Sodium | | 340.73 |
| Calcium (2:1) | | 675.56 |

TABLE 3-continued
| Salt | Salt Structure | M.W. |
|---|---|---|
| Ethanolamine | 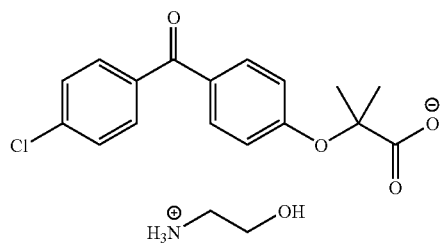 | 379.83 |
| Meglumine | 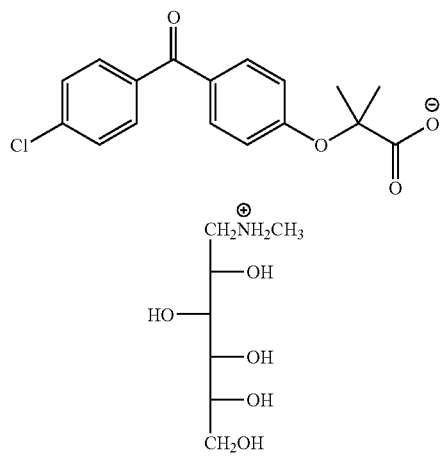 | 513.96 |
| L-Lysine | 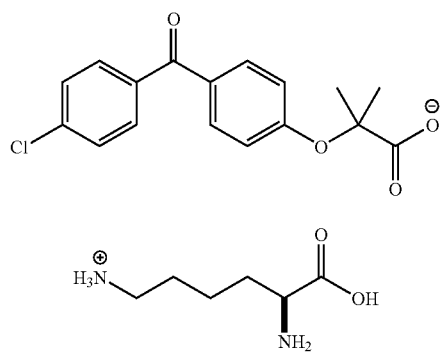 | 464.94 |
| Piperazine (2:1) | 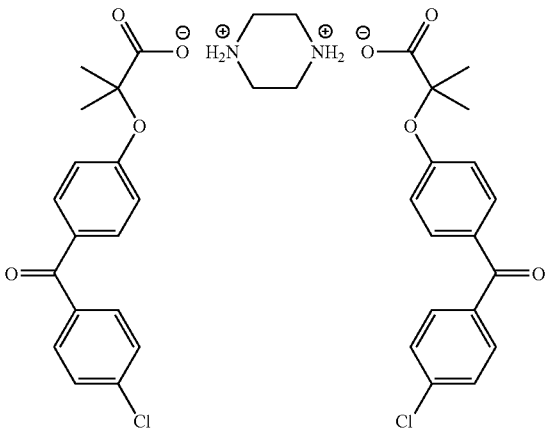 | 723.64 |

TABLE 4

| Salt/Form | Melting Point Range (° C.) | PLM[1] |
|---|---|---|
| Choline | 209–211 | Crystalline |
| Diethanolamine | 142–144 | Crystalline |
| Tromethamine | 198–204 | Crystalline |
| Sodium | 236 | Crystalline |
| Calcium (2:1) | 242–246* | Crystalline |
| Ethanolamine | 121–123 | Crystalline |
| Meglumine | 114–116 | Crystalline |
| L-Lysine | 163–169 | Crystalline |
| Piperazine (2:1) | 215–217 | Crystalline |
| Fenofibric Acid Form I | 175–176 | Crystalline |
| Fenofibric Acid Form II | 184–185 | Crystalline |

*Melting point of solid after dehydration and recrystallization peaks
[1]Polarized Light Microscopy

EXAMPLE 28

Solid State Photostability of Fenofibric Acid and its Salts

About 1–4 mg of each of fenofibric acid form I, fenofibric acid form II, choline, diethanolamine, tromethamine, sodium, calcium, ethanolamine, meglumine, L-lysine, and piperazine was weighed into separate 4 mL clear glass vials. The methods for making each of these salts is described in Example 17A (choline), Example 18A (tromethamine), Example 19A (calcium), Example 20 (diethanolamine), Example 21 (L-lysine), Example 22B (piperazine), Example 23 (ethanolamine), Example 24 (meglumine) and Example 25 (sodium). Fenofibric acid form I was made as described in Example 26A and can be purchased from Labo Test, Niederschoena, Germany. Fenofibric acid form II was obtained from Synkem, Chenove Cedex, France and can be made as described in Example 26B and can also be made pursuant to U.S. Pat. No. 4,072,705, which is hereby incorporated by reference.

The vials were sealed with PTFE lined caps, and divided into 2 groups with at least three replicates in each group. The first group was wrapped in aluminum foil to serve as controls. Samples and controls were placed inside a light exposure chamber (SUNTEST CPS+, Atlas Material Testing Technology, LLC, Chicago, Ill.) where temperature was maintained at 25° C. Exposure conditions were selected to follow the "Guideline for the Photostability Testing of New Drug Substances and Products" (International Conference on Harmonization. Federal Register 1997; 65(95):27115–22.) The light source is a xenon arc lamp filtered through window glass to mimic indoor daylight (ISO 10977 ID65). The total light exposure (300–800 nm wavelength) was 19460 kJ/m$^2$ over 18 hours. At the end of the light exposure, all samples and controls were removed and analyzed by HPLC using the conditions shown below in Table 6. The photostability results are shown below in Table 5.

TABLE 5

| Sample | Recovery %[a] (±Standard Deviation, n = 3) |
|---|---|
| Fenofibric acid, Form I | 40.9 ± 8.3 |
| Fenofibric acid, Form II | 99.0 ± 0.6 |
| Choline salt | 97.4 ± 3.5 |
| Calcium salt | 98.8 ± 1.6 |
| Diethanolamine salt | 98.8 ± 0.5 |
| Sodium salt | 98.0 ± 2.2 |
| Meglumine salt | 85.7 ± 2.6 |
| L-Lysine salt | 94.4 ± 2.2 |
| Ethanolamine salt | 98.1 ± 1.8 |
| Tromethamine salt | 98.6 ± 1.2 |
| Piperazine salt | 100.4 ± 1.0 |

[a]Normalized with controls as 100%.

TABLE 6

| HPLC Conditions | |
|---|---|
| Column: | Waters Symmetry Shield (Available from Waters, Milford, Mass.) RP18, 5 μm, 250 mm × 4.6 mm |
| Flow Rate: | approximately 1 mL/min |
| Injection Volume: | 10 μL |
| Column Temperature: | approximately 35° C. |
| Detector/Wavelength: | UV at 286 nm |
| Mobile Phase: | ACN:Acidified Water, pH 2.5 (60:40) |
| Run time: | 60 minutes |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

We claim:

1. A salt of fenofibric acid selected from the group consisting of choline, ethanolamine, diethanolamine, piperazine, calcium and tromethamine.

2. The salt of claim 1 wherein said salt is choline.

3. The salt of claim 1 wherein said salt is ethanolamine.

4. The salt of claim 1 wherein said salt is diethanolamine.

5. The salt of claim 1 wherein said salt is piperazine.

6. The salt of claim 1 wherein said salt is calcium.

7. The salt of claim 1 wherein said salt is tromethamine.

8. A pharmaceutical formulation in a form of a molecular dispersion comprising:
   i. a salt of fenofibric acid selected from the group consisting of choline, ethanolamine, diethanolamine, piperazine, calcium and tromethamine; and
   ii. a binder component comprising at least one enteric binder.

9. The formulation of claim 8 further comprising a physiologically acceptable excipient.

10. The formulation as claimed in claim 8, wherein the enteric binder is an enteric polymer.

11. The formulation as claimed in claim 10, wherein the enteric polymer is selected from hydroxypropylmethylcellulose phthalate, hydroxypropylmethylcellulose acetate succinate, carboxymethylethylcellulose, cellulose acetate phthalate, cellulose acetate trimellitate and carboxymethylcellulose sodium.

12. The formulation as claimed in claim 10, wherein the enteric polymer is a copolymer of (meth)acrylic acid and at least one alkyl (meth)acrylic acid ester.

13. The formulation as claimed in claim 12, wherein the alkyl (meth)acrylic acid ester is methyl methacrylate.

14. The formulation as claimed in claim 8, wherein the formulation comprises about 5 to about 60% by weight of said salt and about 20 to about 95% by weight of a binder component.

15. The formulation of claim 9, wherein the formulation comprises about 1 to about 60% of a physiologically acceptable excipient.

* * * * *